(12) United States Patent
Ohta (10) Patent No.: US 7,527,808 B2
(45) Date of Patent: May 5, 2009

(54) AMORPHOUS CEFDITOREN PIVOXIL COMPOSITION AND PROCESS FOR PRODUCING THE SAME

(75) Inventor: Masato Ohta, Yokohama (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 400 days.

(21) Appl. No.: 10/475,729

(22) PCT Filed: Apr. 26, 2002

(86) PCT No.: PCT/JP02/04278

§ 371 (c)(1),
(2), (4) Date: Oct. 24, 2003

(87) PCT Pub. No.: WO02/087588

PCT Pub. Date: Nov. 7, 2002

(65) Prior Publication Data

US 2004/0115272 A1    Jun. 17, 2004

(30) Foreign Application Priority Data

Apr. 26, 2001    (JP)    ............................. 2001-130290

(51) Int. Cl.
*A61K 9/14*    (2006.01)
*A61K 9/20*    (2006.01)
*A61K 9/48*    (2006.01)

(52) U.S. Cl. .................. 424/489; 424/451; 424/452; 424/464; 424/465

(58) Field of Classification Search .................. None
See application file for complete search history.

(56) References Cited

U.S. PATENT DOCUMENTS

| | | | |
|---|---|---|---|
| 4,673,564 A * | 6/1987 | Kawata et al. .............. 514/781 |
| 5,989,832 A * | 11/1999 | Trias et al. .................... 435/7.2 |
| 5,994,340 A * | 11/1999 | Maiti et al. .................. 514/192 |
| 6,136,336 A | 10/2000 | Tanaka et al. |
| 6,267,989 B1 * | 7/2001 | Liversidge et al. .......... 424/489 |
| 2001/0046526 A1 * | 11/2001 | Greenfelder ................. 424/779 |
| 2003/0059471 A1 * | 3/2003 | Compton et al. ............ 424/489 |
| 2004/0033258 A1 * | 2/2004 | Koike .......................... 424/465 |

FOREIGN PATENT DOCUMENTS

| EP | 695548 | 2/1996 |
|---|---|---|
| EP | 1051978 | 7/1999 |
| EP | 1051978 A1 * | 11/2000 |
| JP | 8-40907 | 2/1996 |
| JP | 10-265380 | 10/1998 |
| JP | 2001-131071 | 5/2001 |
| WO | 99/34832 | 7/1999 |
| WO | WO 9965919 A1 * | 12/1999 |

OTHER PUBLICATIONS

Masato Ohta et al., "Evaluation of Physicochemical Stability of Amorphous Cefditoren Pivoxil, Using Modulated-Temperature Differential Scanning Calorimetry", Journal of Pharmaceutical Science and Technology, Japan, vol. 60, No. 2, pp. 160-165, XP009090316, ISSN: 0372-7629, 2000.
Supplementary European Search Report issued Oct. 25, 2007.

* cited by examiner

*Primary Examiner*—S. Tran
(74) *Attorney, Agent, or Firm*—Wenderoth, Lind & Ponack, L.L.P.

(57) ABSTRACT

An objective of the present invention is to provide an amorphous cefditoren pivoxil composition possessing excellent stability and dissolvability and to provide a production process of the amorphous composition. The amorphous cefditoren pivoxil composition according to the present invention comprises cefditoren pivoxil and a pharmaceutically acceptable organic polymeric compound, wherein the composition is obtainable by grinding a crystalline cefditoren pivoxil in the presence of a pharmaceutically acceptable organic polymeric compound to convert the crystalline cefditoren pivoxil to an amorphous substance.

7 Claims, 11 Drawing Sheets

AMORPHOUS CEFDITOREN PIVOXIL COMPOSITION AND PROCESS FOR PRODUCING THE SAME

BACKGROUND OF THE INVENTION

1. Field of the Invention

The present invention relates to an amorphous cefditoren pivoxil composition, which is highly stable and has improved dissolvability, a pharmaceutical composition for oral administration comprising said amorphous composition, and a process for producing the same.

2. Background Art

Cefditoren pivoxil is a novel prodrug in which a pivaloyloxymethyl group has been attached by an ester bond to a carboxylic acid at the 4-position of an antibiotic cefditoren having a wide antimicrobial spectrum, namely (+)-(6R,7R)-7-[(Z)-2-(2-aminothiazol-4-yl)-2-methoxyiminoacetamido]-3-[(Z)-2-(4-methylthiazol-5-yl)ethenyl]-8-oxo-5-thia-1-azabicyclo[4.2.0]oct-2-ene-2-carboxylic acid, known also in the chemical name of [6R-[3(Z),6α,7β(Z)]]-7-[[(2-amino-4-thiazolyl)(methoxyimino)acetyl]amino]-3-[2-(4-methyl-5-thiazolyl)ethenyl]-8-oxo-5-thia-1-azabicyclo [4.2.0]oct-2-ene-2-carboxylic acid, for the purpose of imparting excellent oral absorption to cefditoren. Cefditoren pivoxil is represented by formula (I):

(I)

Further, cefditoren pivoxil is known in the name of (−)-(6R,7R)-7-[(Z)-2-(2-aminothiazol-4-yl)-2-methoxyiminoacetamido]-3-[(Z)-2-(4-methylthiazol-5-yl)ethenyl]-8-oxo-5-thia-1-azabicyclo[4.2.0]oct-2-ene-2-carboxylic acid 2,2-dimethylpropionyloxymethyl ester. Another chemical name of this compound is [6R-[3(Z),6α,7β(Z)]]-7-[[(2-amino-4-thiazolyl)(methoxyimino)acetyl]amino]-3-[2-(4-methyl-5-thiazolyl)ethenyl]-8-oxo-5-thia-1-azabicyclo [4.2.0]oct-2-ene-2-carboxylic acid (2,2-dimethyl-1-oxopropoxy)methyl ester).

It is generally known that cefditoren pivoxil, when used as an oral preparation, has a very broad antimicrobial spectrum while enjoying low toxicity and is very useful for the therapy and prophylaxis of diseases induced by gram-positive and gram-negative bacteria (see, for example, Japanese Patent Publication No. 64503/1991, U.S. Pat. No. 4,839,350, and European Patent No. 175610).

Crystals of cefditoren pivoxil are known to have high purity, high heat stability, and, in addition, satisfactory stability even when stored under high humidity conditions (see WO 98/12200 and U.S. Pat. No. 6,294,669).

Crystals of cefditoren pivoxil, however, have low solubility in water and thus have not been very suitable for oral administration of cefditoren pivoxil per se.

In general, in medicinal compounds sparingly soluble in water, the solubility or dissolution rate thereof is known to greatly affect the absorption of these compounds in vivo. Accordingly, many reports about how to improve the dissolvability of the medicinal compounds sparingly soluble in water were presented.

An example of these methods is to convert a medicinal compound to an amorphous substance having improved dissolvability which is then utilized as preparations. Amorphous substances are generally known to have smaller energy necessary for dissolution, that is, a higher level of dissolvability, than the corresponding crystalline substances.

Therefore, the conversion of a crystalline form of cefditoren pivoxil sparingly soluble in water to an amorphous substance having high water solubility leads to the expectation of improved usefulness of cefditoren pivoxil in the therapy of diseases.

An example of a method for converting the crystalline form of cefditoren pivoxil sparingly soluble in water to an amorphous substance having high water solubility is described in WO 99/34832 and U.S. Pat. No. 6,342,493. In this method, the crystalline cefditoren pivoxil is dissolved in an acidic aqueous solution containing a water-soluble polymeric additive, the acidic aqueous solution is then neutralized to coprecipitate cefditoren pivoxil together with the water-soluble polymeric additive, and the precipitate is then collected, washed, and dried. According to this method, a yellow-colored powdery composition comprising solid particles of an intimate mixture of an amorphous form of cefditoren pivoxil having a high level of dissolvability in water and high heat stability with the water-soluble polymeric additive (0.5 to 5%) can be provided.

This method, however, involves many steps and thus requires process control and a relatively lot of time. Therefore, the above method is not necessarily satisfactory from the viewpoint of production efficiency.

Thus, a composition of an amorphous form of cefditoren pivoxil having a combination of stability and dissolvability, which are desired in orally administrable pharmaceutical compositions, is desired.

SUMMARY OF THE INVENTION

The present inventors have now found that an amorphous cefditoren pivoxil composition can be easily prepared by grinding a crystalline cefditoren pivoxil in the presence of a pharmaceutically acceptable organic polymeric compound to convert the crystalline cefditoren pivoxil to an amorphous substance and that the amorphous composition has excellent stability and dissolvability. The present invention has been made based on such finding.

Accordingly, an object of the present invention is to provide a composition of an amorphous form of cefditoren pivoxil, which has excellent stability and, at the same time, has excellent dissolvability, and a production process of the amorphous composition.

According to one aspect of the present invention, there is provided an amorphous cefditoren pivoxil composition comprising cefditoren pivoxil and a pharmaceutically acceptable organic polymeric compound, wherein the composition is obtainable by grinding a crystalline cefditoren pivoxil in the presence of a pharmaceutically acceptable organic polymeric compound to convert said crystalline cefditoren pivoxil to an amorphous substance.

According to another aspect of the present invention, there is provided a pharmaceutical composition for oral administration, comprising the above amorphous cefditoren pivoxil composition and a pharmaceutically acceptable carrier.

According to a further aspect of the present invention, there is provided a process for producing an amorphous cefditoren pivoxil composition comprising cefditoren pivoxil and a pharmaceutically acceptable organic polymeric compound, said process comprising the step of grinding a crystalline cefditoren pivoxil in the presence of a pharmaceutically acceptable organic polymeric compound to convert said crystalline cefditoren pivoxil to an amorphous substance.

According to the present invention, an amorphous cefditoren pivoxil composition having excellent stability and a high level of dissolvability can be easily prepared. By virtue of excellent stability and good dissolvability, the amorphous cefditoren pivoxil composition according to the present invention, when orally administered, is therapeutically very useful.

Further, the amorphous cefditoren pivoxil composition according to the present invention is less likely to be recrystallized.

DETAILED DESCRIPTION OF THE INVENTION

Amorphous Cefditoren Pivoxil Composition

As described above, the amorphous cefditoren pivoxil composition according to the present invention comprises cefditoren pivoxil and a pharmaceutically acceptable organic polymeric compound, wherein the composition is obtainable by grinding a crystalline cefditoren pivoxil in the presence of a pharmaceutically acceptable organic polymeric compound to convert the crystalline cefditoren pivoxil to an amorphous substance.

The term "amorphous" as used herein means a solid state in which cefditoren pivoxil molecules gathered together with a pharmaceutically acceptable organic polymeric compound without forming crystals having a regular spacial configuration, more specifically a solid state in which the amorphous form can be confirmed by conventional powder X-ray diffractometry. Specifically, a crystalline cefditoren pivoxil exhibits a sharp diffraction peak, whereas, as with the amorphous cefditoren pivoxil (a ground product of cefditoren pivoxil per se), the amorphous composition according to the present invention does not substantially exhibit any diffraction peak. This generally means that the amorphous composition according to the present invention is in an amorphous state.

More specifically, the term "amorphous" means a state that, for example, in a powder X-ray diffraction diagram measured by the method as described in test 1 in an evaluation test which will be described later, the graph is in the so-called "halo pattern" form having substantially no sharp peak.

The expression "converted to an amorphous substance" as used herein includes the case where cefditoren pivoxil exists in a substantially completely amorphous form and, in addition, the case where a finely divided crystalline form of cefditoren pivoxil also exists as a part of cefditoren pivoxil.

In the present invention, the term "crystalline cefditoren pivoxil" means cefditoren pivoxil in a crystalline form in which substantially all cefditoren pivoxil molecules have a regular spacial configuration. In the present invention, the crystalline cefditoren pivoxil may be a commercially available one. Alternatively, the crystalline cefditoren pivoxil could be easily prepared by a person having ordinary skill in the art according to a method described, for example, in WO 98/12200 or U.S. Pat. No. 6,294,669.

In the present invention, the "pharmaceutically acceptable organic polymeric compound" is not particularly limited so far as the organic polymeric compound is pharmaceutically acceptable and does not inhibit the activity of cefditoren pivoxil and conversion of cefditoren pivoxil to an amorphous substance. Preferably, the "pharmaceutically acceptable organic polymeric compound" is selected from the group consisting of crystalline cellulose, hydroxypropylcellulose, hydroxypropylmethylcellulose, hydroxypropylmethylcellulose phthalate, hydroxypropylmethylcellulose acetate succinate, methylcellulose, carboxymethylcellulose, carboxymethylethylcellulose, povidone, polyethylene glycol, ethyl acrylate-methyl methacrylate copolymer, methacrylic acid copolymer, propylene glycol alginate, casein and its salts, pullulan, and carageenan. These compounds may be used as a mixture of two or more.

In a more preferred embodiment of the present invention, the "pharmaceutically acceptable organic polymeric compound" is crystalline cellulose, casein and its salt, hydroxypropylmethylcellulose, or a mixture thereof, more preferably casein and its salt, hydroxypropylmethylcellulose, or a mixture thereof.

The salt of casein is, for example, an alkali metal salt or an alkaline earth metal salt, preferably an alkali metal salt, more preferably a sodium salt or a potassium salt.

In the present invention, the amount of the pharmaceutically acceptable organic polymeric compound used is not particularly limited. The weight ratio of cefditoren pivoxil to the pharmaceutically acceptable organic polymeric compound, i.e., cefditoren pivoxil/pharmaceutically acceptable organic polymeric compound, is typically 95/5 to 5/95, preferably 10/90 to 5/95.

The production process of an amorphous cefditoren pivoxil composition according to the present invention comprises the step of grinding a crystalline cefditoren pivoxil in the presence of a pharmaceutically acceptable organic polymeric compound to convert the crystalline cefditoren pivoxil to an amorphous substance.

"Grinding" may be carried out with any device so far as the device can crush and attrite the crystalline cefditoren pivoxil to prepare fine particles and can convert cefditoren pivoxil to an amorphous substance. Typically, a grinding machine/crusher is used.

The grinding machine/crusher is not particularly limited so far as it can mechanically crush and attrite the crystalline cefditoren pivoxil to prepare fine particles, and examples thereof include vibration ball mills, rotary ball mills, vibration rod mills, hammer mills, pin mills, and Micros. Further, in the present invention, an extruder may be used for grinding.

The grinding time necessary for conversion of the crystalline cefditoren pivoxil to an amorphous substance varies depending upon the type of the grinding machine/crusher used, grinding power, the total weight of the object, the type and proportion of additives and the like. In general, the grinding time is in the range of several tens of minutes to several hours. For example, the grinding time necessary for conversion of the crystalline cefditoren pivoxil to an amorphous substance, in the case where 3.0 g (total amount) of a mixture of a crystalline cefditoren pivoxil and a pharmaceutically acceptable organic polymeric compound is ground in a vibration rod mill, for example, model TI-200 manufactured by CMT, is at least about 30 min. Further, the grinding time necessary for conversion of cefditoren pivoxil to an amorphous substance, in the case where 3.0 g (total amount) of a mixture of a crystalline cefditoren pivoxil and a pharmaceutically acceptable organic polymeric compound is ground in a ball mill, is at least about 30 min. The above grinding can easily provide an amorphous composition having a combination of good stability with good dissolvability.

In another preferred embodiment of the present invention, the amorphous cefditoren pivoxil composition substantially exhibits neither an exothermic peak nor an endothermic peak in a DSC (differential scanning calorimetry) curve at a temperature rise rate of 10° C./min as determined with a differential scanning calorimeter. Further, preferably, the amorphous cefditoren pivoxil composition according to the present invention does not have any clear melting point at a temperature of 120° C. or above.

Use of Composition/Pharmaceutical Composition

The amorphous cefditoren pivoxil composition according to the present invention may be used as antibacterial agents. Bacteria referred to herein include, for example, gram-positive bacteria such as *staphylococcus* and *streptococcus*, gram-negative bacteria such as *Escherichia coli, Branhamella catarrhalis, Klebsiella, Proteus,* and *Haemophilus influenzae*, and *anaerobes* such as *Peptostreptococcus, Propionibacterium acnes,* and *Bacteroides*.

Further, the composition according to the present invention is useful for the prophylaxis or therapy of diseases induced by gram-positive bacteria or gram-negative bacteria.

The amorphous cefditoren pivoxil composition according to the present invention as such may be used as a drug. Alternatively, the amorphous cefditoren pivoxil composition according to the present invention may be used as bulk powder for the manufacture of a pharmaceutical composition comprising the amorphous cefditoren pivoxil composition and a pharmaceutically acceptable carrier.

The pharmaceutical composition according to the present invention may be used by any administration route so far as the high level of dissolvability of the amorphous cefditoren pivoxil composition can be utilized, for example, by oral administration, intraoral administration, parenteral administration, topical administration, or rectal administration. The pharmaceutical composition according to the present invention is preferably administered orally. Further, the pharmaceutical composition according to the present invention can be used as antibacterial agents.

The dosage form of the pharmaceutical composition suitable for oral administration is not particularly limited and may be properly selected depending upon the use of the pharmaceutical composition. Examples of dosage forms include powders, granules, tablets, pills, and capsules. The pharmaceutical composition according to the present invention may be prepared by a conventional method using a pharmaceutically acceptable carrier.

Pharmaceutically acceptable carriers include, for example, excipients, binders, disintegrants, and colorants. They may be used solely or in a combination of two or more depending upon the form of the pharmaceutical composition.

Excipients include, for example, lactose, corn starch, sucrose, glucose, kaolin, talc, crystalline cellulose, mannitol, precipitated silicic anhydride, sodium chloride, calcium carbonate, and L-cysteine.

Binders include, for example, gelatinized starch, partially gelatinized starch, methylcellulose, carboxymethylcellulose, hydroxypropylcellulose, hydroxypropylmethylcellulose, hydroxypropylmethylcellulose phthalate, glycerin fatty acid esters, polyglycerin fatty acid esters, povidone, pullulan, dextrin, and gum arabic.

Disintegrants include, for example, sodium alginate, agar powder, carboxymethylcellulose calcium, starches, croscarmellose, Crospovidone, and polyoxysorbitan fatty acid esters.

Colorants include, for example, titanium oxide, iron oxide red, and tar coloring matter.

Preparations manufactured by mixing a cefditoren pivoxil bulk powder with, for example, cyclodextrin (Japanese Patent Publication No. 78234/1994 and European Patent No. 339465), hydroxypropylcellulose (Japanese Patent Laid-Open Publication No. 17866/1995 and European Patent Laid-Open Publication No. 629404), and sodium caseinate (WO 97/13516 and U.S. Pat. No. 5,958,915) are known as cefditoren pivoxil preparations. Accordingly, based on descriptions of these documents, a person having ordinary skill in the art could properly select excipients, binders, disintegrants, colorants and the like and could easily manufacture medicinal preparations having substantially the same or superior biological activity by a conventional method.

The content of the amorphous cefditoren pivoxil composition in the pharmaceutical composition according to the present invention may be properly selected depending upon the dosage form.

The dose may be appropriately determined depending on various conditions, for example, the age, weight, gender, disease, and severity of condition of patients. The dose effective for the treatment of infectious diseases is, for example, typically 25 to 2,000 mg/kg, preferably 50 to 1,000 mg/kg, in terms of the amount of cefditoren pivoxil. This dose may be administered at a time daily or divided doses of several times daily.

The amorphous cefditoren pivoxil composition according to the present invention may be administered in combination with other medicines, for example, other antibacterial agents. The amorphous cefditoren pivoxil composition according to the present invention and the other medicines may be administered simultaneously or over time.

According to another aspect of the present invention, there is provided a method for the therapy of an infectious disease, comprising the step of administering a therapeutically effective amount of an amorphous cefditoren pivoxil composition to a human or a mammal other than the human.

EXAMPLE

The following Example further illustrates but does not limit the present invention.

Production Example

Amorphous cefditoren pivoxil compositions 1 to 7 according to the present invention were prepared as follows.

Amorphous Composition 1

A crystalline cefditoren pivoxil (0.3 g, manufactured by Meiji Seika Kaisha Co., Ltd.) and 2.7 g of sodium caseinate (manufactured by New Zealand Dairy Board) (cefditoren pivoxil/sodium caseinate weight ratio=10/90) were placed in a grinding vessel made of aluminum oxide. The mixture was ground in a vibration rod mill (model TI-200, manufactured by CMT) for 30 min to prepare amorphous composition 1.

Amorphous Composition 2

A crystalline cefditoren pivoxil (0.3 g, manufactured by Meiji Seika Kaisha Co., Ltd.) and 2.7 g of crystalline cellulose (manufactured by Asahi Chemical Industry Co., Ltd.) (cefditoren pivoxil/crystalline cellulose weight ratio=10/90) were placed in a grinding vessel made of aluminum oxide.

a physical mixture (without grinding) prepared by merely mixing crystalline cefditoren pivoxil and organic polymeric compound together without grinding; and organic polymeric compound per se (without grinding).

The individual evaluated samples were as shown in Table 2 below.

TABLE 2

| Sample name | | Weight ratio of cefditoren pivoxil to organic polymeric compound | | Organic polymeric compound used |
|---|---|---|---|---|
| | | Cefditoren pivoxil | Organic polymeric compound | |
| a | Crystalline cefditoren pivoxil | 100 | 0 | |
| b | Amorphous cefditoren pivoxil | 100 | 0 | |
| $c_1$ | Physical mixture of cefditoren pivoxil with organic polymeric compound | 10 | 90 | Sodium caseinate |
| $p_1$ | Amorphous composition 1 | 10 | 90 | Sodium caseinate |
| $z_1$ | — | 0 | 100 | Sodium caseinate |
| $c_2$ | Physical mixture of cefditoren pivoxil with organic polymeric compound | 10 | 90 | Crystalline cellulose |
| $p_2$ | Amorphous composition 2 | 10 | 90 | Crystalline cellulose |
| $z_2$ | — | 0 | 100 | Crystalline cellulose |
| $p_3$ | Amorphous composition 3 | 95 | 5 | Hydroxypropylmethylcellulose |
| $q_3$ | Amorphous composition 4 | 70 | 30 | Hydroxypropylmethylcellulose |
| $r_3$ | Amorphous composition 5 | 50 | 50 | Hydroxypropylmethylcellulose |
| $s_3$ | Amorphous composition 6 | 30 | 70 | Hydroxypropylmethylcellulose |
| $t_3$ | Amorphous composition 7 | 5 | 95 | Hydroxypropylmethylcellulose |
| $z_3$ | — | 0 | 100 | Hydroxypropylmethylcellulose |

The mixture was ground in a vibration rod mill (model TI-200, manufactured by CMT) for 30 min to prepare amorphous composition 2.

Amorphous Compositions 3 to 7

Mixtures of a crystalline cefditoren pivoxil (manufactured by Meiji Seika Kaisha Co., Ltd.) and hydroxypropylmethylcellulose (manufactured by The Shin-Etsu Chemical Co., Ltd.) were prepared each in a total amount of 3.0 g at a weight ratio specified in Table 1 below. The mixtures were placed in a grinding vessel made of aluminum oxide and were ground in a vibration rod mill (model TI-200, manufactured by CMT) for 30 min to prepare amorphous compositions 3 to 7.

TABLE 1

| | Weight ratio of crystalline cefditoren pivoxil/hydroxypropylmethylcellulose |
|---|---|
| Amorphous composition 3 | 95/5 |
| Amorphous composition 4 | 70/30 |
| Amorphous composition 5 | 50/50 |
| Amorphous composition 6 | 30/70 |
| Amorphous composition 7 | 5/95 |

Evaluation Test

The amorphous compositions prepared in the above production example were evaluated for the following items. The following four controls were provided:

crystalline cefditoren pivoxil (without grinding);

crystalline cefditoren pivoxil as such was ground and rendered amorphous;

Test 1: Powder X-ray Diffraction

Each sample shown in Table 2 including amorphous compositions 1 to 7 was analyzed by powder X-ray diffractometry with an X-ray diffraction device (model RINT 2200, manufactured by Rigaku Corporation).

Figure 1:
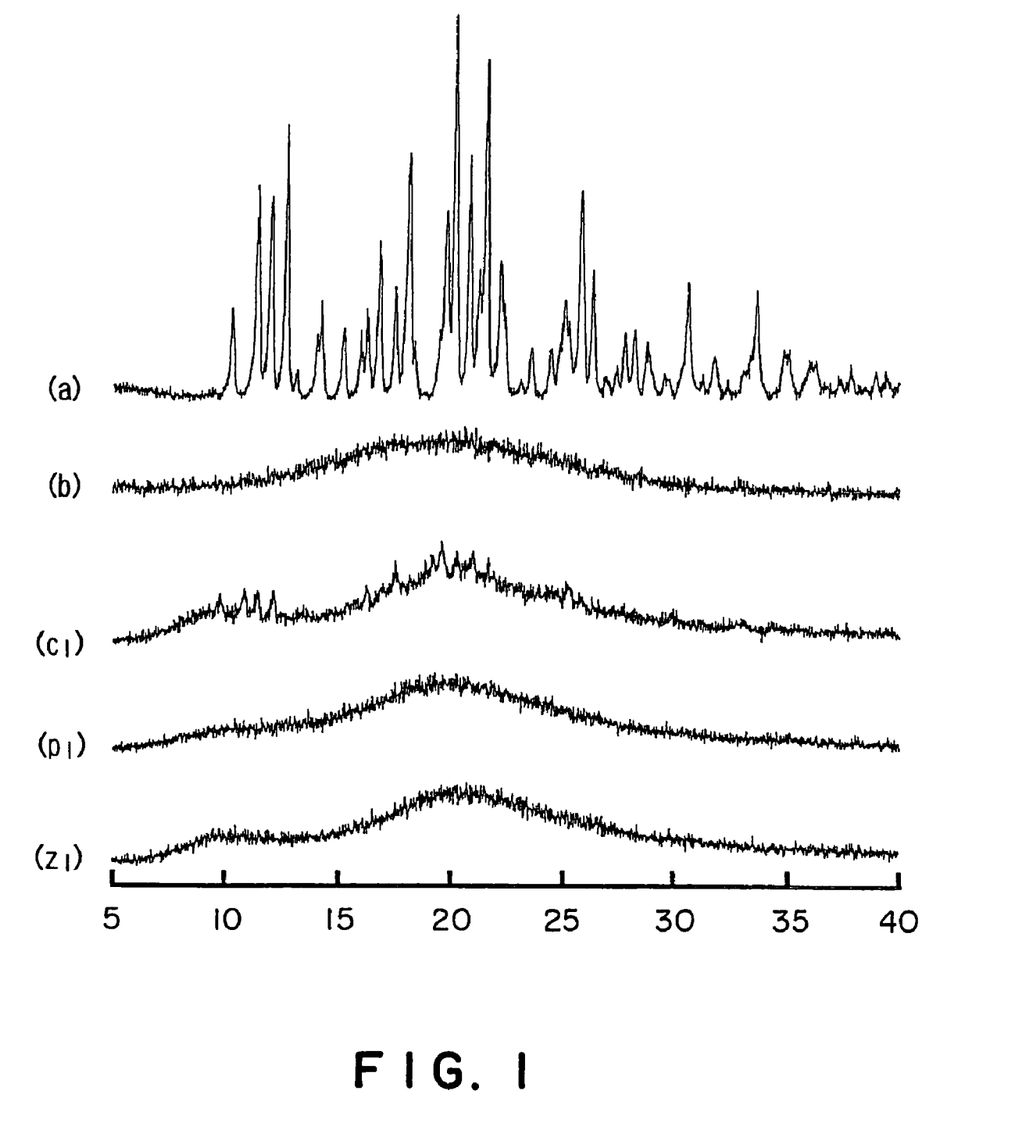
FIGS. 1 to 3 are powder X-ray diffraction diagrams as measured for each sample which show the results of test 1 in the working example, wherein alphabetical characters attached to respective graphs represent sample names shown in Table 2.
Figure 2:
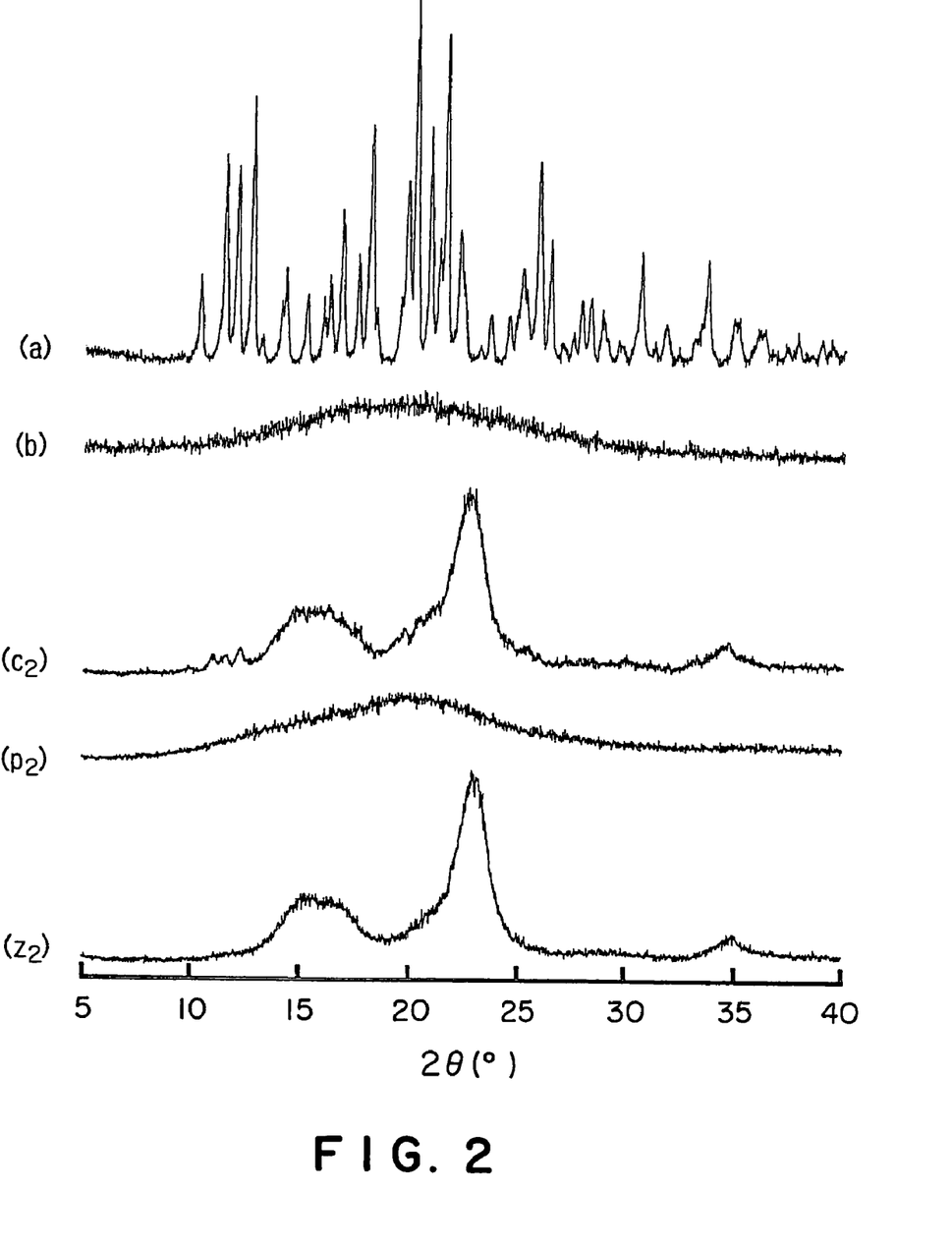
Figure 3:
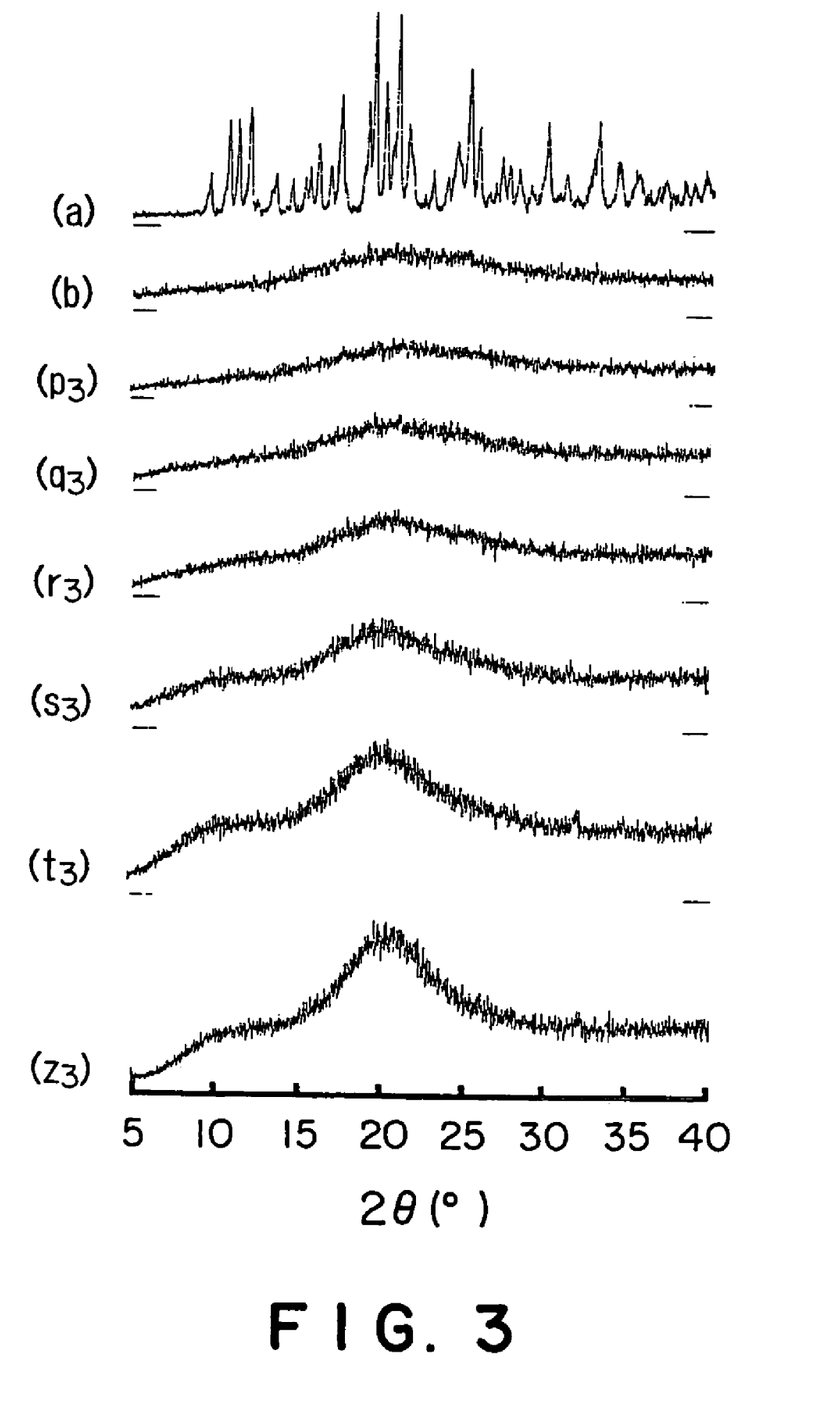

The results were as shown in FIGS. 1 to 3.

Samples, which have not been ground, did not exhibit any halo pattern and exhibited a sharp diffraction peak or peaks characteristic of respective samples, indicating that the samples were not converted to an amorphous substance.

All the ground samples (amorphous compositions 1 to 7 and the ground product of cefditoren pivoxil per se) exhibited a halo pattern, indicating that cefditoren pivoxil was converted to an amorphous substance.

Test 2: Thermal Analysis

The samples shown in Table 2 were examined for stability against heat with a differential scanning calorimeter (model DSC 3100, manufactured by MAC Science).

Figure 4:
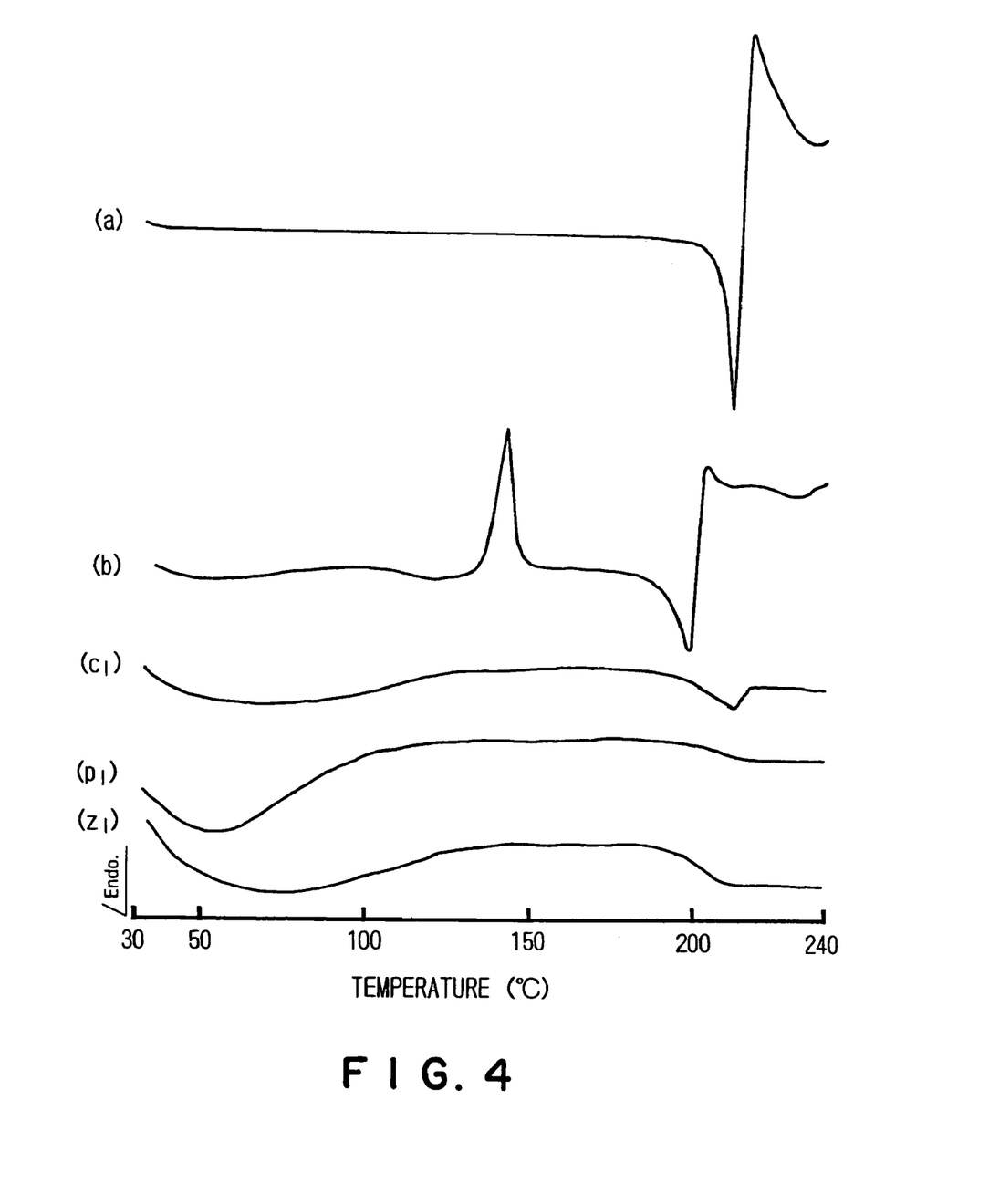
FIGS. 4 to 6 are DSC curves measured for each sample which show the results of test 2 in the working example, wherein alphabetical characters attached to respective graphs represent sample names shown in Table 2.
Figure 5:
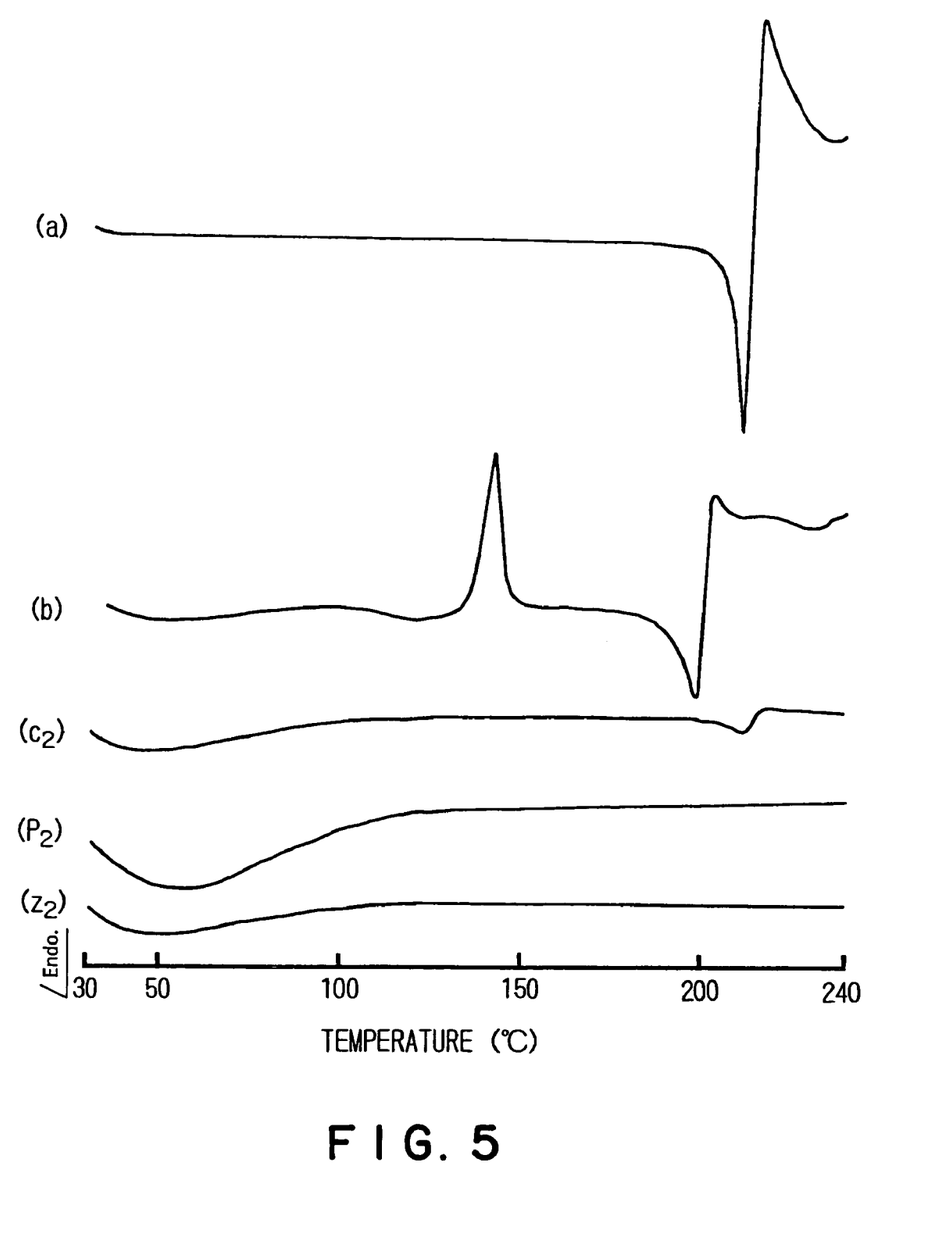
Figure 6:
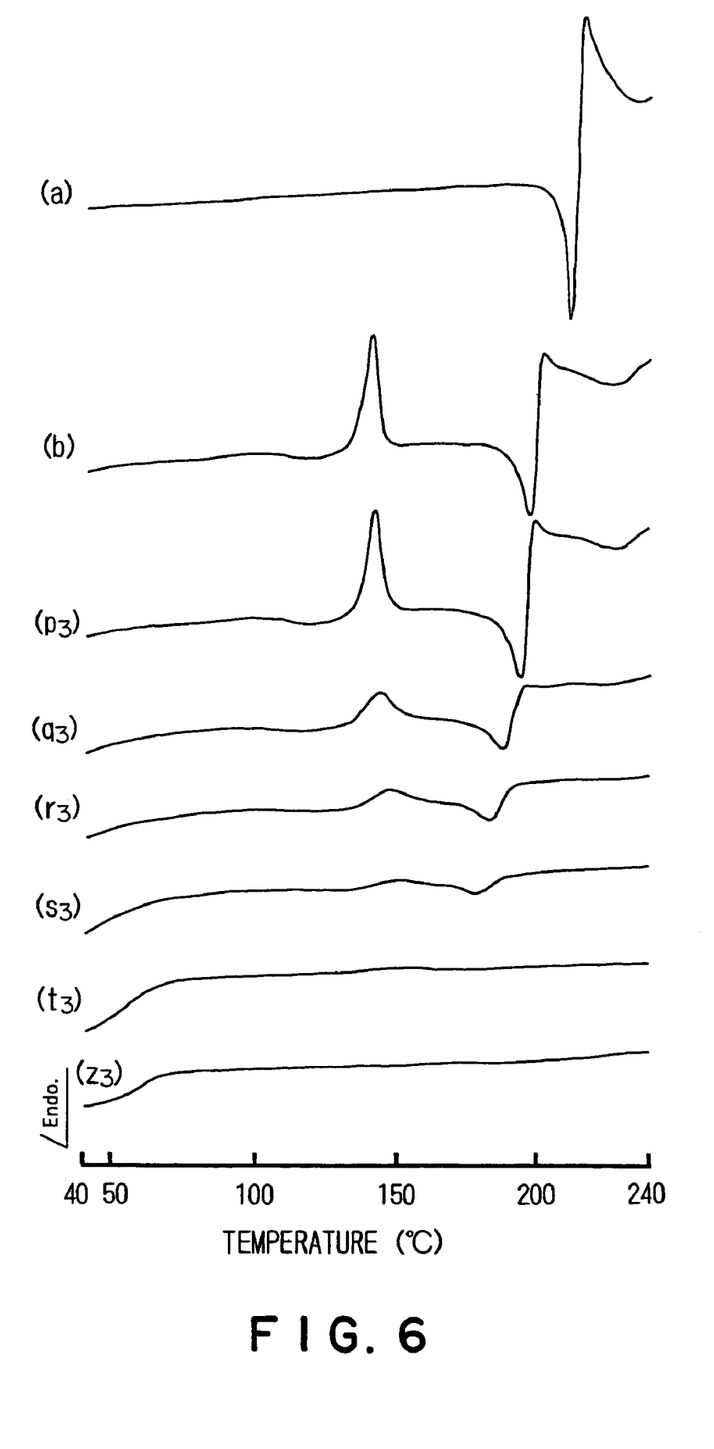

As a result, DSC curves (temperature rise rate 10° C./min) as shown in FIGS. 4 to 6 were obtained.

For the crystalline cefditoren pivoxil, in a DSC curve at a temperature rise rate of 10° C./min, a fusion endothermic peak with decomposition was observed at 206 to 215.7° C. For the amorphous cefditoren pivoxil (a ground product of cefditoren pivoxil per se), in a DSC curve at a temperature rise rate of 10° C./min, an exothermic peak was observed at a temperature around 140° C., and cefditoren pivoxil was transferred to a crystalline state. Upon further heating, an endothermic peak was observed at a temperature around 200° C., and cefditoren pivoxil was melted.

For amorphous compositions 1 and 2, none of the above peaks was observed, suggesting that the amorphous compositions were stable.

For amorphous compositions 3 to 7, the exothermic peak shifted toward a higher temperature side with increasing the content of hydroxypropylmethylcellulose and became gentle. The endothermic peak also became gentle with increasing the content of hydroxypropylmethylcellulose, and, finally, no peak became detected. This suggests that hydroxypropylmethylcellulose suppresses the crystallization of the amorphous form of cefditoren pivoxil.

Test 3: Infrared Absorption Spectrum

An infrared absorption spectrum of each sample shown in Table 2 was examined. For each sample, an infrared absorption spectrum measured by a potassium bromide disk method (see The Japanese Pharmacopoeia, Fourteenth Edition, Part I, General Tests "34. Infrared absorption spectrophotometry") with a Fourier transform infrared spectroscopic analyzer (model FT/IR-230, manufactured by JASCO).

Figure 7:
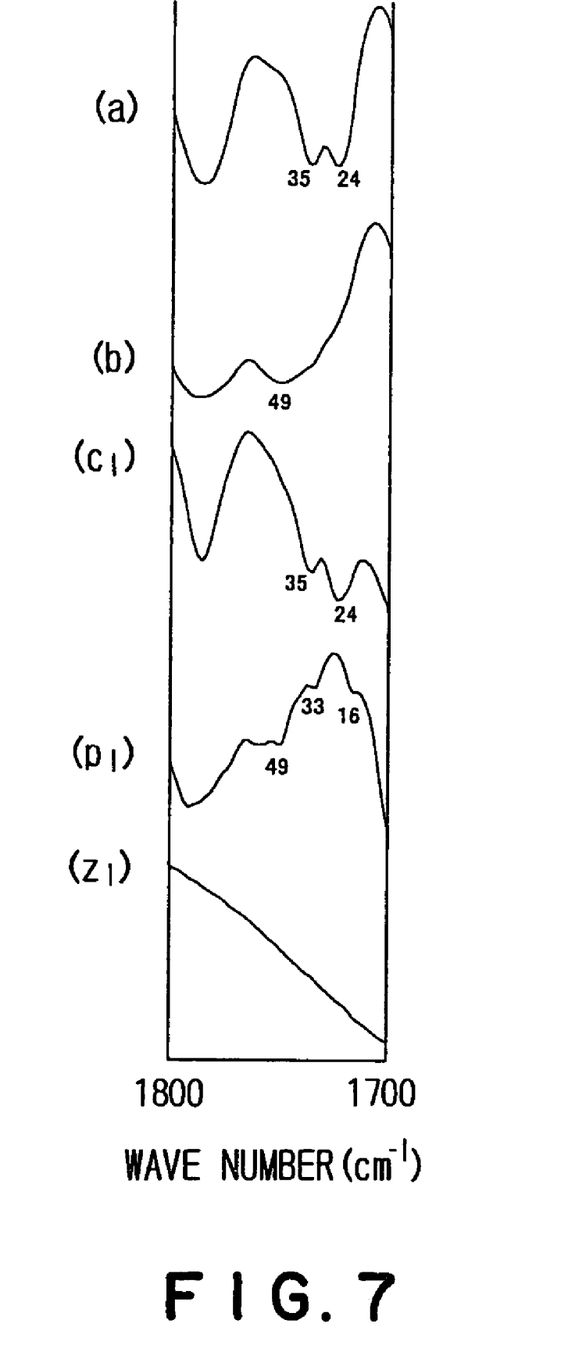
FIGS. 7 to 9 are infrared absorption spectra as measured for each sample which show the results of test 3 in the working example, wherein alphabetical characters attached to respective graphs represent sample names shown in Table 2.
Figure 8:
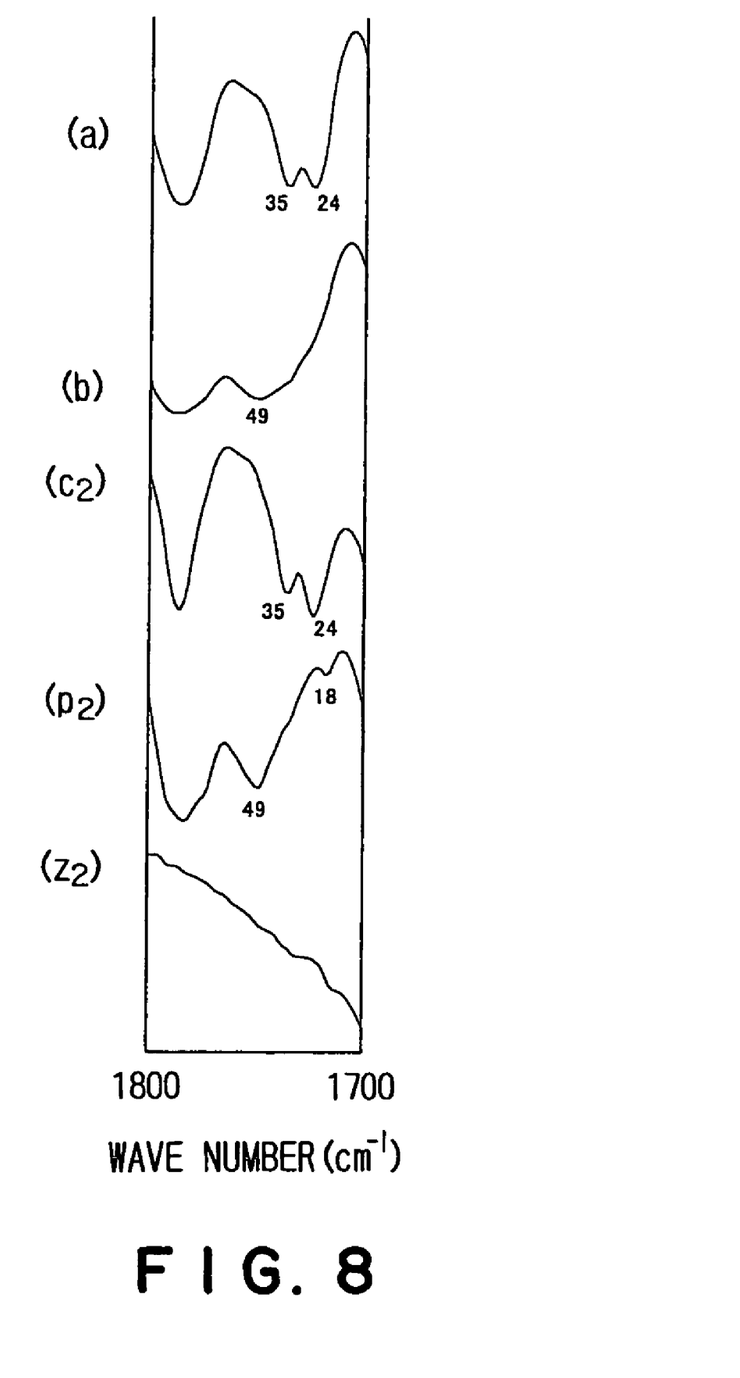
Figure 9:
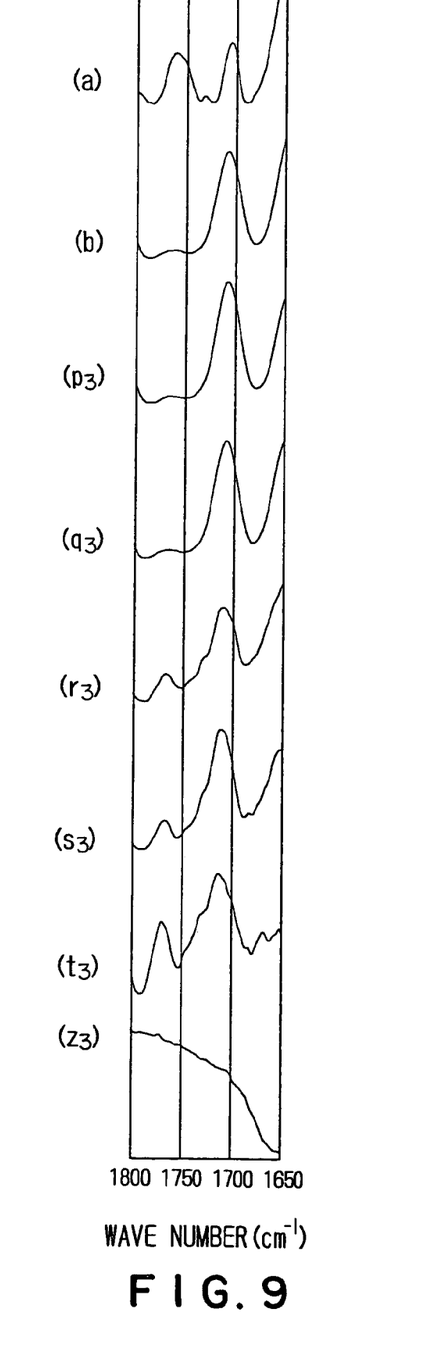

The results were as shown in FIGS. 7 to 9.

As compared with the crystalline cefditoren pivoxil, for both amorphous compositions 1 and 2, a shift of a peak derived from carbonyl stretching vibration of ester in cefditoren pivoxil toward a smaller wave number side was observed. This suggests that the carbonyl group of ester in cefditoren pivoxil, together with the amide group in sodium caseinate or the hydroxyl group in the crystalline cellulose, formed a hydrogen bond. Based on this, it is estimated that this hydrogen bond contributes to the suppression of the crystallization of cefditoren pivoxil.

For amorphous compositions 3 to 7, independently of the content of hydroxypropylmethylcellulose, any peak derived from carbonyl stretching vibration of ester derived from the crystal was not observed. Based on this, it is estimated that amorphous compositions 3 to 7 are in a homogeneous amorphous state.

Test 4: Dissolution Test

For each sample shown in Table 2, a dissolution test (see The Japanese Pharmacopoeia, Fourteenth Edition, Part I, General Tests "56. Dissolution test, Method 2") was carried out in a second fluid specified in the Japanese Pharmacopoeia (a fluid prepared by adding 118 mL of a 0.2 mol/L sodium hydroxide reagent solution and water to 250 mL of a 0.2 mol/L potassium dihydogenphosphate reagent solution; the amount of the water being a sufficient amount to bring the total volume of the fluid to 1,000 mL). The fluid with the sample dissolved therein was sampled at fixed intervals of time and was filtered through a glass filter G-4 manufactured by TOYAMA SANGYO Co., Ltd., and the amount of dissolved cefditoren pivoxil was then quantitatively determined at a measuring wavelength of 272 nm with a spectrophotometer (UV-160, manufactured by Shimadzu Seisakusho Ltd.

Figure 10:
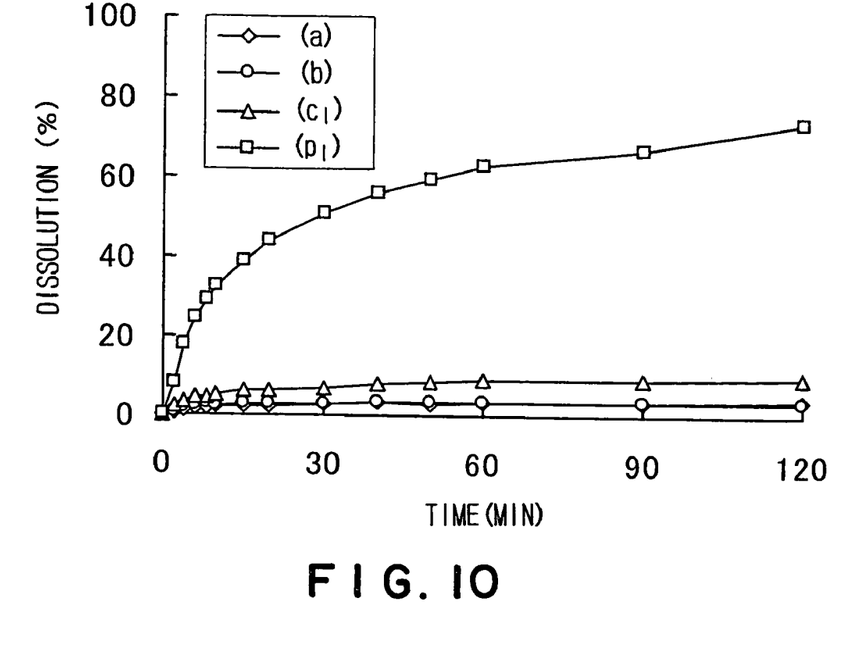
FIGS. 10 to 12 are dissolution curves for cefditoren pivoxil as measured for each sample which show the results of test 4 in the working example, wherein alphabetical characters attached to respective graphs represent sample names shown in Table 2.
Figure 11:
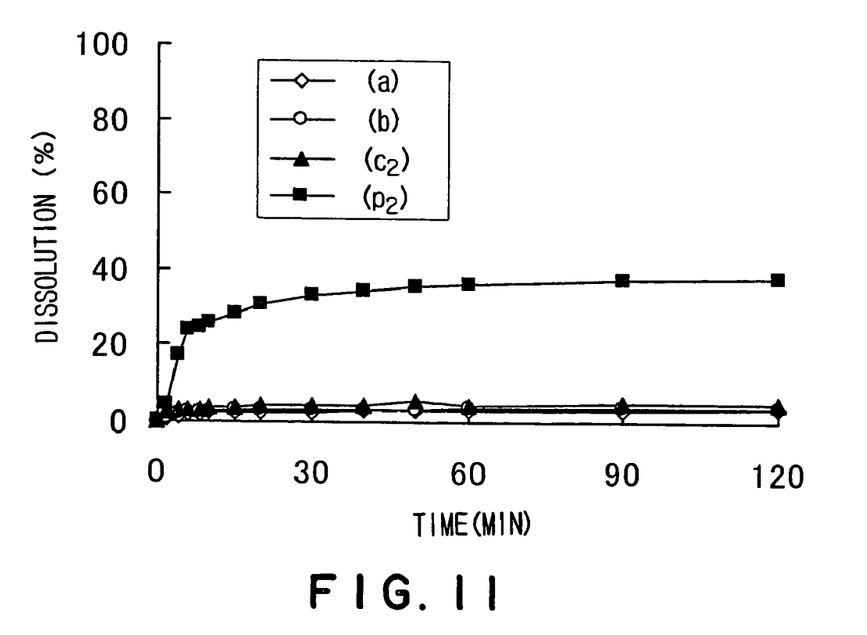
Figure 12:
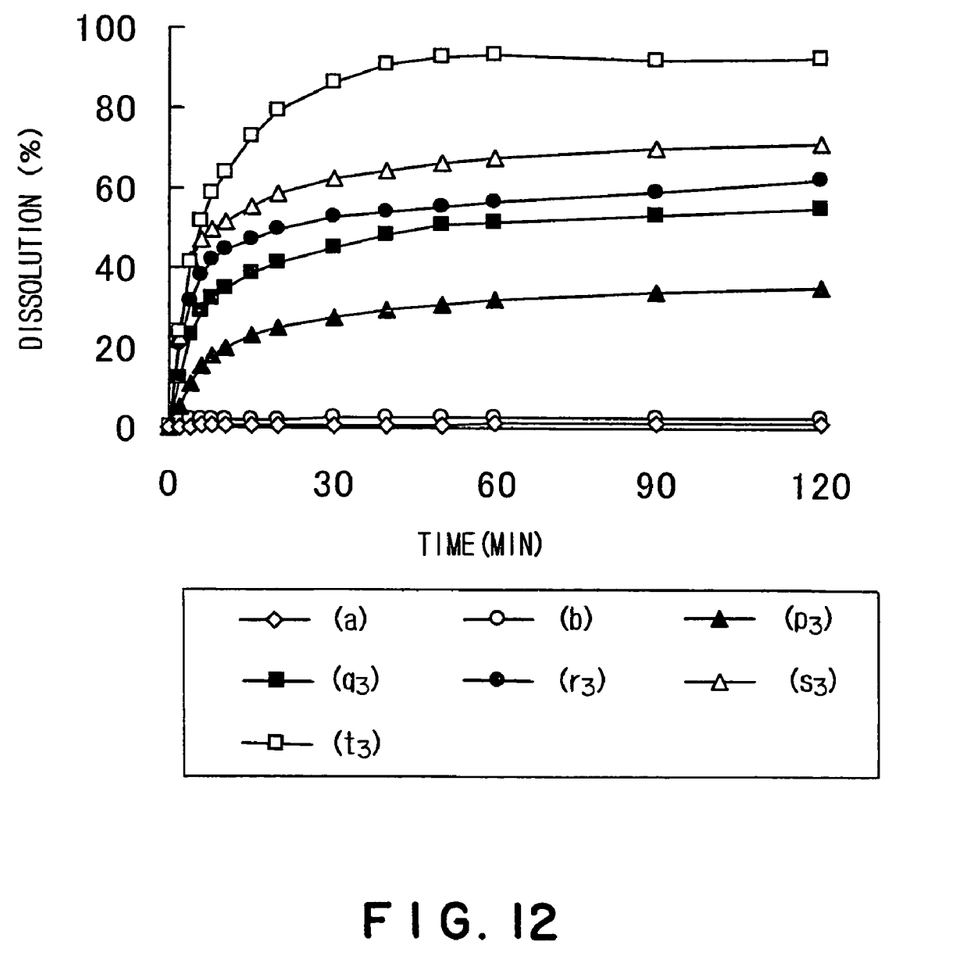

Based on the results, dissolution curves were prepared and are shown in FIGS. 10 to 12.

For the crystalline cefditoren pivoxil and the amorphous cefditoren pivoxil (a ground product of cefditoren pivoxil per se), there was substantially no difference in dissolvability. For amorphous compositions 1 and 2, a significant improvement in dissolvability was observed over the physical mixture. For amorphous compositions 3 to 7, the dissolvability enhanced with enhancing the content of hydroxypropylmethylcellulose.

Preparation Examples

Preparation 1

Amorphous composition 1 (130 g) and 260 g of corn starch were mixed together to give powder preparations.

Preparation 2

Amorphous composition 2 (130 g), 260 g of spray dried lactose, 130 g of croscarmellose sodium, and 3 g of magnesium stearate were added and mixed together, and the mixture was filled into capsules to give 1,000 capsule preparations.

Preparation 3

Amorphous composition 5 (130 g), 260 g of β-cyclodextrin, 5 g of hydroxypropylcellulose, 103 g of D-mannitol, 195 g of malic acid, and 7 g of sucrose fatty acid ester were mixed together to prepare powder as an intimate mixture. The powder as an intimate mixture was wet-granulated and finely subtilized by a conventional method to give subtilized granule preparations.

Preparation 4

Amorphous composition 7 (130 g), 390 g of corn starch, and 480 g of D-mannitol were mixed together to prepare powder as an intimate mixture. The powder as an intimate mixture was wet-granulated by a conventional method to give granule preparations.

The invention claimed is:

1. An amorphous cefditoren pivoxil composition comprising cefditoren pivoxil and a pharmaceutically acceptable organic polymeric compound, wherein the composition is obtainable by grinding a crystalline cefditoren pivoxil in the presence of a pharmaceutically acceptable organic polymeric compound to convert said crystalline cefditoren pivoxil to an amorphous substance, wherein the pharmaceutically acceptable organic polymeric compound is hydroxypropylmethylcellulose, and wherein the weight ratio of cefditoren pivoxil/pharmaceutically acceptable organic polymeric compound is 5/95 to 95/5.

2. The composition according to claim 1, for use as an antibacterial agent.

3. A pharmaceutical composition for oral administration, comprising said amorphous cefditoren pivoxil composition according to claim 1 and a pharmaceutically acceptable carrier.

4. A process for producing an amorphous cefditoren pivoxil composition comprising cefditoren pivoxil and a pharmaceutically acceptable organic polymeric compound, said process comprising the step of:

grinding a crystalline cefditoren pivoxil in the presence of a pharmaceutically acceptable organic polymeric compound to convert said crystalline cefditoren pivoxil to an amorphous substance, wherein the pharmaceutically acceptable organic polymeric compound is hydroxypropylmethylcellulose, and wherein the weight ratio of cefditoren pivoxil/pharmaceutically acceptable organic polymeric compound is 5/95 to 95/5.

5. The process according to claim 4, wherein the grinding is carried out by grinding 3.0 g in total of the cefditoren pivoxil and the pharmaceutically acceptable organic polymeric compound in a vibration rod mill for not less than 30 min.

6. A method for the treatment of a disease induced by gram-positive bacteria or gram-negative bacteria, comprising the step of administering a therapeutically effective amount of the composition according to claim 1 to a human or a mammal other than the human.

7. A pharmaceutical composition for oral administration, comprising said amorphous cefditoren pivoxil composition according to claim 2 and a pharmaceutically acceptable carrier.

* * * * *